United States Patent
Oberdorfer et al.

(10) Patent No.: US 6,419,886 B1
(45) Date of Patent: Jul. 16, 2002

(54) TRAY

(75) Inventors: Harald Oberdorfer, Säntisstrasse 10, CH-9707 Mosnang; Heinz Suter, Pfäffikon, both of (CH)

(73) Assignee: Harald Oberdorfer, Mosnang (CH)

( * ) Notice: Subject to any disclaimer, the term of this patent is extended or adjusted under 35 U.S.C. 154(b) by 0 days.

(21) Appl. No.: 09/623,770

(22) PCT Filed: Mar. 6, 1998

(86) PCT No.: PCT/CH98/00093

§ 371 (c)(1),
(2), (4) Date: Nov. 17, 2000

(87) PCT Pub. No.: WO99/44717

PCT Pub. Date: Sep. 10, 1999

(51) Int. Cl.[7] ................................................. A61L 2/06
(52) U.S. Cl. ...................... 422/300; 422/292; 422/297; 220/324; 220/371
(58) Field of Search ........................... 422/292, 26, 34, 422/297, 300; 210/232; 220/324, 371

(56) References Cited

U.S. PATENT DOCUMENTS

| | | | |
|---|---|---|---|
| 4,661,326 A | * | 4/1987 | Schainholz .................. 422/310 |
| 4,671,873 A | * | 6/1987 | Keller ........................ 210/232 |
| 4,701,234 A | | 10/1987 | Rogemont et al. |
| 4,783,321 A | * | 11/1988 | Spence ........................ 422/300 |

FOREIGN PATENT DOCUMENTS

| | | |
|---|---|---|
| DE | 3340963 | 1/1985 |
| DE | 19627044 | 1/1998 |
| DE | 196 27 044 A | * 1/1998 |

* cited by examiner

*Primary Examiner*—Robert J. Warden, Sr.
*Assistant Examiner*—Sean E. Conley
(74) *Attorney, Agent, or Firm*—Martin A. Farber

(57) ABSTRACT

For use in medical trays the filtering flat material (2) has to be such that no micro-organisms can penetrate through it. In order to arrange such a filter (1) for achieving closure of a tray's partial surface including through openings which ensures sterility, a closed sealing line, which surrounds the through openings, is formed in the area of each flat partial surface having through openings, along which two tray parts to be assembled and including co-operating clamping surfaces enable clamping the seal (3) of the filter (1). By the elasticity of the seal (3) sufficiently good closure is ensured even by small clamping pressure and even with not precisely plane clamping surfaces. The bond of the seal (3) to the filtering flat material (2) has the additional advantage that the filter (1) can also be arranged at a lower surface by pressing its seal (3) into a corresponding groove and does not loosen due to gravity.

7 Claims, 3 Drawing Sheets

TRAY

FIELD AND BACKGROUND OF THE INVENTION

The invention relates to a tray.

When using medical implements which possibly might contact blood in an investigation or operation of a live body, these implements have to be sterile up to their employment. After use they are cleaned and/or desinfected, sterilised and stored. The resulting manipulation labour should be as small as possible. From DE 196 27 044 A1, a tray is known which can be inserted both into a washing device as a wash basket and into a sterilisation device as a sterilising tray. Before sterilising, the tray is closed at top and bottom by an inserted filter. To this end, pieces of a steam permeable, germs retaining filter paper are inserted into slots, and are optionally held by a clamping facility. When transporting the implements to washing, thermal desinfection and to sterilisation after use, the same need no longer to be taken by hand, but can remain within the tray. Now, it has turned out that insertion of the filters is awkward. In order to protect the filter against mechanical influences, a covering element has to be put on in some cases. Moreover, in spite of the filter papers inserted, sterile storage of implements within the tray is not ensured, because complete closure around the filter to the inner space of the tray cannot safely be realised.

Trays available on the market are known which comprise a perforated area in a central bottom region. Outside the perforated area, threaded bolts project from the bottom of the tray into its receiving region at the corner points of a rectangle. Filter paper is inserted between the threaded bolts and covers the perforated area. Subsequently, a perforated metal sheet is laid upon the filter paper aligned with the perforation of the perforated area. The threaded bolts penetrate bores of the perforated metal sheet. Now, the perforated metal sheet can be pressed against the tray bottom by nuts on the threaded bolts. By tightly clamping the filter paper, any exchange of a gas or steam between the inner space of the tray and the environment can only be effected through the filter paper. In this way, sterile storing within the tray is made possible. It has turned out, however, that the expenditure for material, production and manipulation is very high due to the additionally inserted perforated metal sheet and the awkward manner of fastening. In addition, this approach is limited to insertion of the filter paper from above onto a perforated area which is on bottom at least during insertion. This approach is not suited for a wash basket in accordance with DE 196 27 044 A1, because the implements had to be removed after washing and before the filter paper could be inserted from above.

SUMMARY OF THE INVENTION

The object of the invention consists in providing a tray at which a flat perforated area can be closed by flat filter material with small expenditure in such a way that any exchange of gas and steam between the inner space of the tray and the environment can only be effected through the filter paper. Sterile storing within the tray should be ensured over an extend period of time.

Within the scope of the present invention, it has been recognised that a seal has to be connected to the flexible, flat filter material. This seal extends preferably in a marginal area of the flexible, flat filter material along a closed line. The filter material has to be such that no micro-organisms can penetrate it. In order to arrange such a filter for achieving a closure, which ensures sterility, on a partial surface of the tray having through holes, it is sufficient that a closed sealing line is formed around the through openings and to enable clamping the seal of the filter along the parts of the tray to be interconnected by means of co-operating clamping surfaces. By the elasticity of the seal a sufficiently good closure is ensured even by small clamping pressure and even with not precisely plane clamping surfaces. Any costly screwing down a perforated plate can be omitted.

The connection of the seal and the flat filter material has the additional advantage that the filter can also be arranged at the lower side by pressing its seal into a groove and does not loosen due to gravity from the lower side. After clamping the seal between the clamping surfaces, the seal prevents any micro-organisms from entering the inner space of the tray around the filter. Due to the possibility of fastening the filter in a groove, a filter can be arranged, for example, at the inner side facing the bottom of a cover member which has a perforated area. The cover together with the filter is then put, for example, onto the closed periphery of a wash basket so that the upper front surface of the periphery presses against the seal of the filter. In this way, the inner space of the wash basket is accessible from above only through the filter. The filter is protected against any damages by the cover surface above. Analogously to the cover, a bottom having a filter inserted can be fastened to the lower front surface of the wash basket's periphery in such a way that the filter seal is clamped between bottom and periphery. In addition, cover and bottom may be formed as identical closing members, thus, being exchangeable. In order not to obstruct the desired penetration of steam through the inserted filter, the arrangement of holes of the closing members and the wash basket are formed congruently one above another. For clamping the closing members under pressure, a clamping device is provided which acts by force optionally between cover and bottom, preferably, however, between one respective closing member and the periphery.

The filter according to the invention having a seal fastened to the flexible, flat filter material can also be employed advantageously in a tray which is used exclusively for sterilisation and, optionally, for subsequent sterile storing. A simple construction of such a sterilisation tray comprises a bottom and/or cover member having a perforated area, a peripheral region of a bottom and/or cover member engaging it positively. By putting a filter according to the invention onto the perforated area in such a way that its seal is pressed by a closed periphery of the one part against a closed partial surface extending around the perforated area of the other part, sterile closure can be ensured.

For producing the filter with a seal a linear closed seal is applied by a foaming appliance onto the flat material held by a device, which is polymerised after application, thereby providing a bond with the flat material. It would be also possible, having some more expenditure, to adhere a sealing ring onto the flat material. Optionally, the flat material cut to the desired size before applying the seal. Preferably, however, the seal is applied to a ribbon of flat material. Severing the individual filters is preferably done later. After applying the seal, preferably at least one temperature treatment is carried out in correspondence with the sealing material applied. When using a silicone foam, a first temperature treatment is carried out, for example, during at least 3, particularly 5, minutes at at least 50° C., particularly, however, at substantially 60° C., and optionally a second temperature treatment during at least 10, particularly 20–30, minutes at at least 120° C., particularly, however, at substantially 140° C. For medical applications preferably silicone foams are used, in particular those which are suitable for food and/or admitted by the Health Department.

Foamed silicone seals have a temperature, moisture and pressure resistance needed for sterilisation. This means that they reassume sufficiently quickly the initial shape after sterilisation. They maintain the desired elasticity and shape even after passing sterilisation procedures several times. Even in cases where they do not provide a tight closure because of some deformation due to temperature or pressure during sterilisation, a tight closure is ensured at least during subsequent storage. Foamed seals have a great deformation capacity and are, therefore, especially suitable for sealing clamping surfaces of high tolerance with respect to plane joining together.

BRIEF DESCRIPTION OF THE DRAWINGS

The figures of the drawings explain the invention with reference to non-limiting embodiments. Therein

DETAILED DESCRIPTION OF THE PREFERRED EMBODIMENT

Figure 1A:
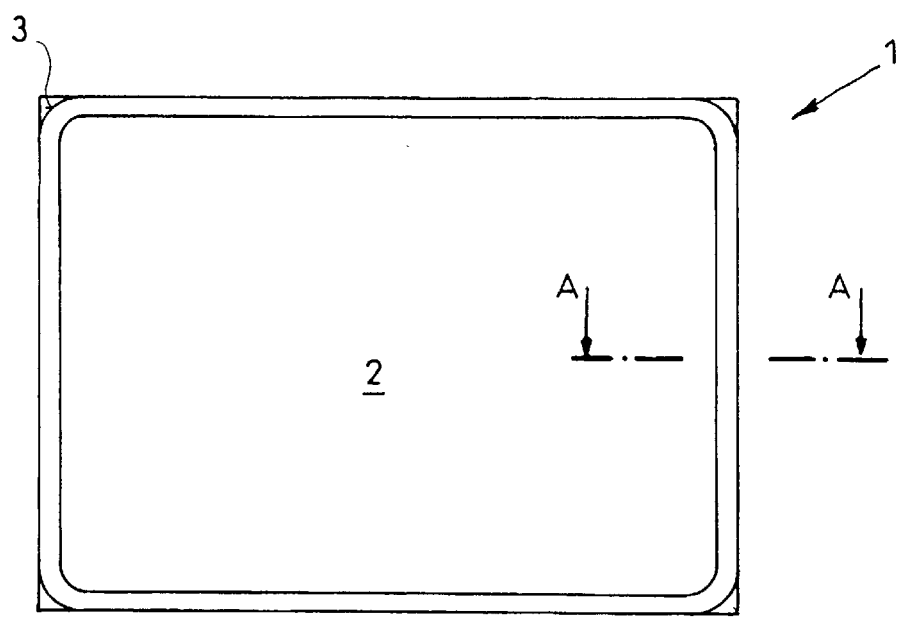
FIG. 1a shows a plan view of a filter and seal.

FIG. 1 shows a filter 1 which comprises a filtering region of flexible flat material 2 and at least one seal 3 extending along a closed line. The seal is secured to the flat material. In this way, an annular seal could be glued on, for example. Preferably, however, the bond is established by foaming the seal directly onto the flat material 2. In this way, the viscous foaming material bonds to the flat material and to its fibres. During subsequent polymerising or curing the bond to the flat material and, of course, the shape of the seal 3 is fixed. The seal 3 extends preferably along the margin of the flat material choosing a rounded pattern at the corner regions.

Figure 1B:
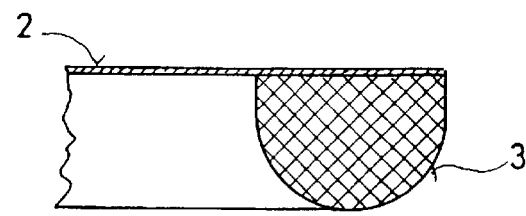
FIG. 1b is a cross-section A—A according to FIG. 1a through a marginal portion of the filter.

According to FIG. 1b, the seal is preferably doughnut-shaped. Flat, ribbon-like seals would, however, also be possible.

Figure 2:
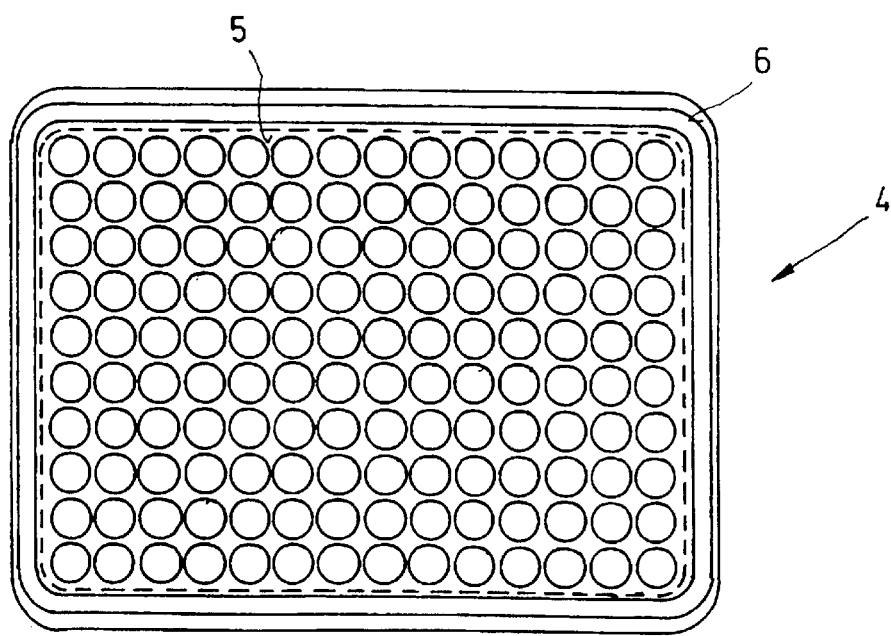
FIG. 2 is a plan view of a tray part (bottom or cover) having a perforated area and a groove extending around.

FIG. 2 shows a tray part 4 having a perforated area 5 and a groove extending around it. In order to shut the perforated area 5 off by a filter 1, the seal 3 of the filter 1 is pressed into the groove 6. For maintaining the filter 1 in any position of the tray part 4, the groove 6 is formed in correspondence with the seal 3. The tray part 4 with the filter 1 inserted is assembled with another tray part in such a way that the seal 3 is situated between two co-operating clamping surfaces. One clamping surface is formed by the groove, and the other one by a front surface of the periphery.

Figure 3:
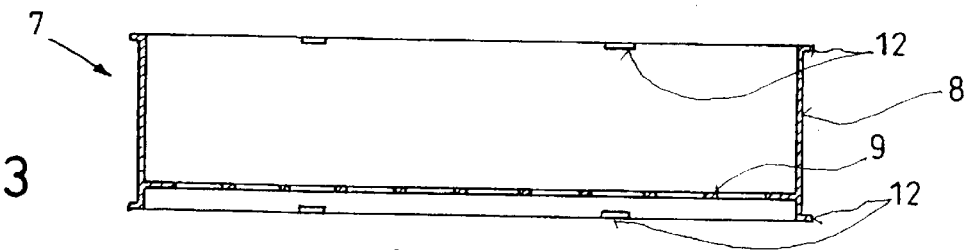
FIG. 3 shows a vertical cross-section of a wash basket.
Figure 4:
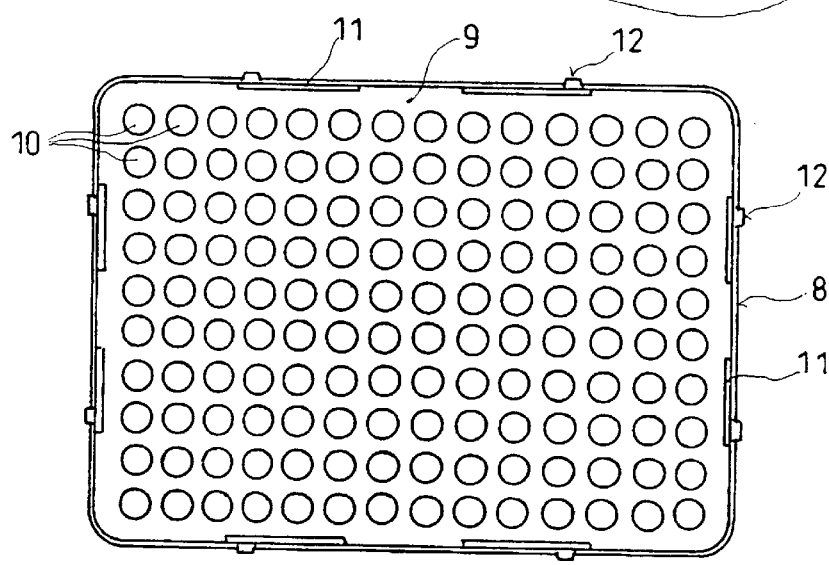
FIG. 4 is a plan view of a wash basket.

FIG. 3 shows a wash basket 7 having a closed peripheral wall 8 which is shut off by a perforated metal sheet 9 within the region of the lower front surface. In the plan view according to FIG. 4, the regular arrangement of holes 10 and the slot-shaped through openings 11 can be seen. Apart from the circular holes, as shown, flattened or cornered holes are also possible. It goes without saying that the holes of the closure elements and also of the bottom of the wash basket can preferably be formed in an analogous way. Straps 12 are formed at the upper and lower peripheral edges and project from the peripheral wall 8 of the wash basket 7 to the exterior. The serve for centring closure members to be put onto the peripheral front sides, on the one hand. On the other hand, the straps 12 of two opposite sides serve as engagement elements of a clamping device for fastening the closure members to the front surfaces of the periphery 8.

Figure 5:
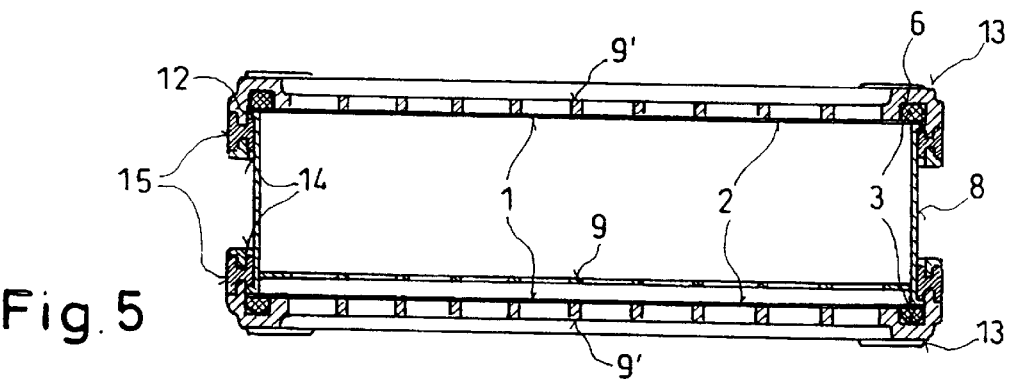
FIG. 5 is a vertical cross-section of a wash basket having closure members and filters put on it at bottom and at top.

FIG. 5 shows a wash basket 7 to which a closure member 13 having a perforated area 9' is fastened each on top and below as a cover and a bottom. A filter 1 having a filter surface 2 and a seal 3 inserted into a groove 6 is provided on each perforated area 9'. The clamping device comprises, apart from the straps 12 of the wash basket 7, shiftable pieces 15, including ramp-like clamping surfaces 14, at two opposite sides of each closure member 13. The same are movably supported in such a way that the clamping surfaces 14 are moveable along the straps 12 in order to achieve a desired position of contact of each closure member 13 on the peripheral wall 8. Upon locking motion of these shiftable pieces 15, the closure member 13 is moved against the peripheral wall 8 by the clamping surfaces 14 in co-operation with the straps 12 so that the seal 3 is firmly pressed between the front surface of the peripheral wall and the groove's bottom of the groove 6.

Figure 6:
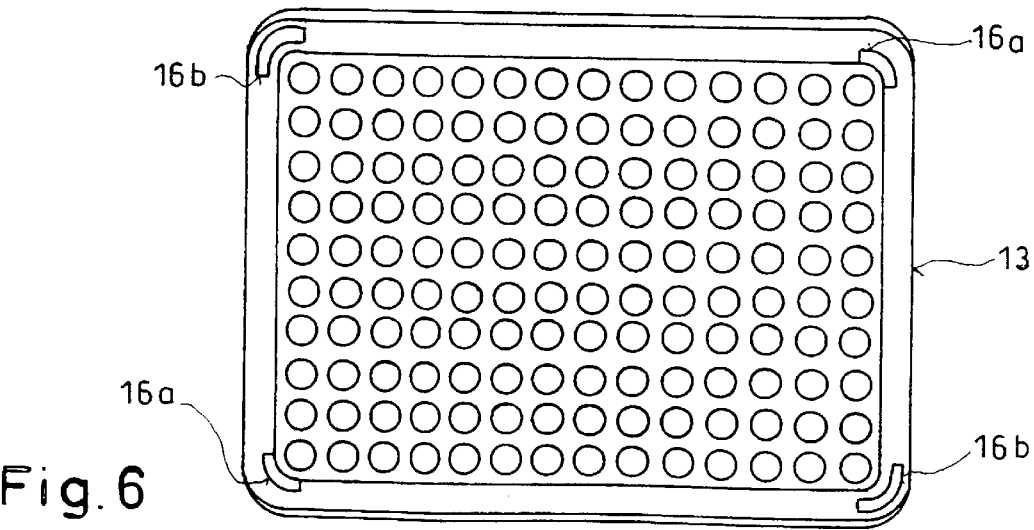
FIG. 6 is a view of a closure member from above.

According to FIG. 6, the closure members 13 include piling aids 16a and 16b in the corner regions of their outer surfaces of which those of one diagonal are arranged within a contact line, those of the other diagonal are outside it. In this way, the outer surfaces of two closure members 13 can engage each other in a substantially slip-free manner. Correspondingly, the trays according to FIG. 5 may be piled on one another. The piling aids 16a, 16b are formed in such a way that a layer-shaped free space remains open between the tray piled up and between the closure surfaces of the closure members 13 which face each other. This free space enables air and steam to circulate between trays which are piled up. Consequently, such trays may be piled up and sterilised in sterilisers without any drawer ledge. In order to facilitate storage of closure members 13, the closure members 13 are constructed such that they can be piled on one another in the same orientation.

The embodiment of the wash basket and the two identical closure members 13 has the advantage that a solution is provided which comprises two different tray parts only and two filters 1 and which enables the use in a cleaning device. and in a sterilising device as well as sterile storing. The wash basket is preferably produced from steel, and the closure members 13 from plastic.

Figure 7:
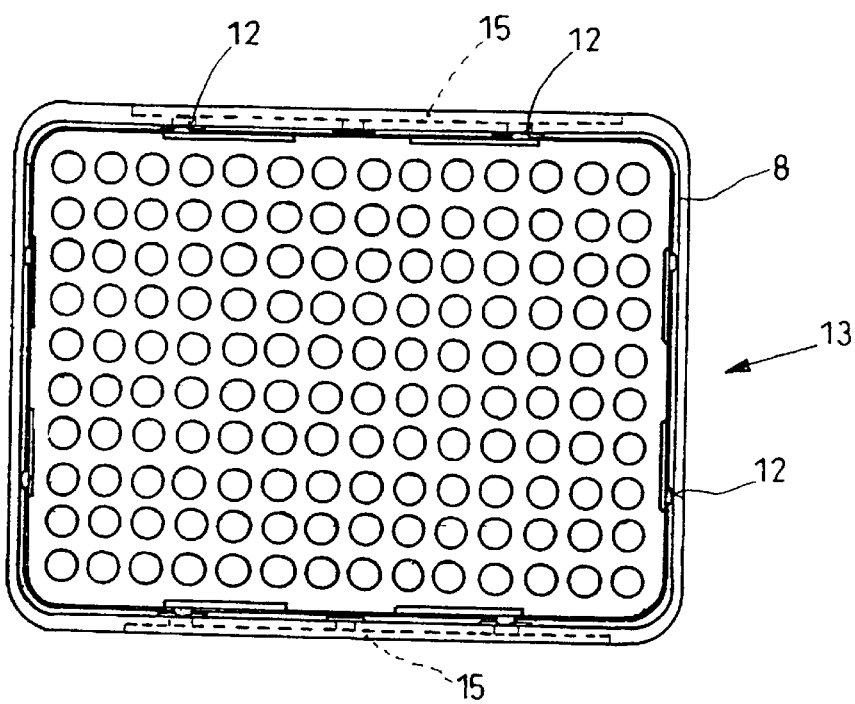
FIG. 7 is a view of a closure member seated on the wash basket's periphery from below.

FIG. 7 points schematically out that the sliders 15 are preferably used along opposite lateral surfaces of a closure member 13. The straps 12 of all sides project against the peripheral surface of the closure member 13 facing the interior for centring the closure member 13. The straps 12 serve also as an enlargement of the bearing area for the seal 3, thus preventing lateral jamming of the seal 3 between the peripheral wall 8 and the 35 peripheral surface of the closure member 13 which faces the interior.

Figure 8:
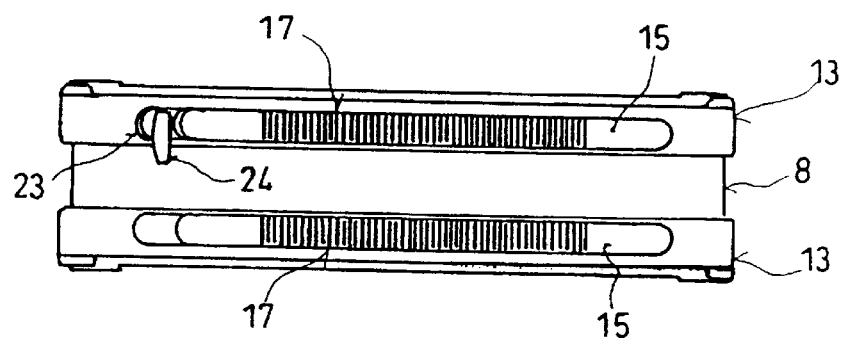
FIG. 8 is a side elevation of a tray's periphery and two closure members.
Figure 9:
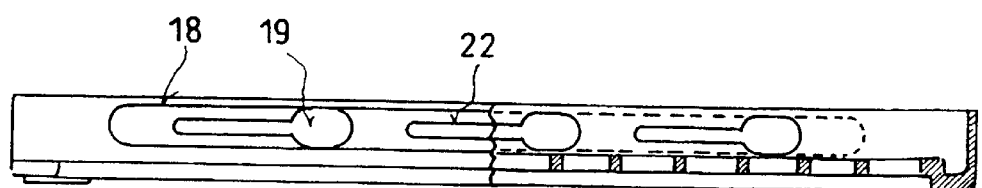
FIG. 9 is a side elevation (left side) and a vertical cross-section (right side) of a closure member without a locking bar.
Figure 10:
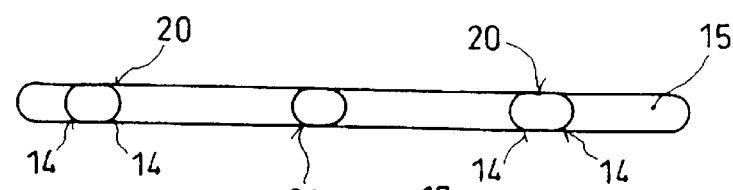
FIG. 10 is a side elevation of a locking bar of a closure member.
Figure 11:
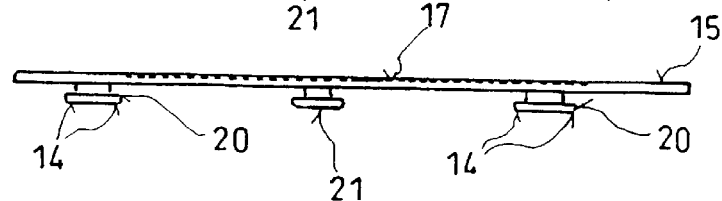
FIG. 11 is a plan view of a locking bar of a closure member.

FIG. 8 shows that handling ribs 17 for actuating the sliders 15 are accessible from outside. The sliders 15, according to FIG. 9, are slidably located in recesses 18 and wall entrances 19. According to FIGS. 10 and 11, the clamping surfaces 14 are formed on clamping pieces 20 projecting through the wall entrances 19 to the interior. Within a central region of the slider 15, optionally a guiding piece 21 for limiting the slider's movement is provided, and a corresponding guiding portion 22 is provided in the closure member.

In order to prevent that a tray containing sterilised instruments can be opened and closed again without being apparent, a safety device is provided. This safety device can be formed in the sense of some leasing or sealing. Preferably a safety piece 23 to be torn away is inserted into the recess 18 beside the slider 15. This safety piece 23 locks the slider 15 in clamping position. The safety piece 23 has to be removed before a closure member 13 can be taken off the wash basket 7. To this end, a splice strap 24 is formed on the safety piece 23. The safety piece 23 and its receiving portion in the closure member 13 are preferably constructed in such a way that some change of the safety piece 23 occurs upon removal which prevents inserting it anew. In this way one can ensure that opening is apparent.

We claim:

1. Tray comprising a wash basket (7) including a closed peripheral wall (8) and in a bottom area a wash part bottom (9) having through-openings, and two mounting areas each for receiving a filter (1) of flexible flat material (2), wherein the filters (1) are located each at a front surface of the peripheral wall (8), two closure members (13) covering the wash basket (7) at the top and at the bottom, and the front surfaces of the peripheral wall (8) together with the closure members (13) forming cooperating clamping surfaces, extending along closed sealing lines and enabling clamping a seal (3) and a filtering flat material (2) in contact with the seal (3), wherein the closure members (13) include each an area with through-openings covered by the filtering flat material (2) and surrounded by the sealing line.

2. Tray according to claim 1, wherein a groove (6) is formed at the closure members (13), or optionally at the wash basket (7), within a region of the sealing line wherein the seal (3), particularly a seal bond to the filtering flat material (2), is to be fixed in said groove (6).

3. Tray according to claim 1, further comprising clamping means which enables pressing the closure members against the corresponding front surface of the peripheral wall (8).

4. Tray according to claim 1, wherein at least one safety piece (23) is insertable enabling opening of the tray only after removal of the safety piece (23), wherein said safety piece (23) is changed by removing which prevents inserting it anew.

5. Tray according to claim 2, further comprising clamping means which enables pressing the closure members against the corresponding front surface of the peripheral wall (8).

6. Tray comprising a wash basket (7) including a closed peripheral wall (8) and in a bottom area a wash part bottom (9) having through-openings, and two mounting areas each for receiving a filter (1) of flexible flat material (2), wherein the filters (1) are located each at a front surface of the peripheral wall (8), two closure members (13) covering the wash basket (7) at the top and at the bottom, and the front surfaces of the peripheral wall (8) together with the closure members (13) forming cooperating clamping surfaces, extending along closed sealing lines and enabling clamping a seal (3) and a filtering flat material (2) in contact with the seal (3), wherein the closure members (13) include each an area with through-openings covered by the filtering flat material (2) and surrounded by the sealing line, the tray further comprising clamping means which enables pressing the closure members against the corresponding front surface of the peripheral wall (8); and wherein the clamping means of the wash basket (7) and of each closure member (13) comprises cooperating engagement elements (12, 20), straps (12) projecting preferably from the peripheral wall (8) of the wash basket (7) to the exterior, and slider members (15) which include clamping surfaces (14) being movably supported such that the clamping surfaces (14) are movable along the straps (12) for achieving a desired contact position of the closure member (13) to the peripheral wall (8) and an elastic deformation of the filter seal (3).

7. Tray comprising a wash basket (7) including a closed peripheral wall (8) and in a bottom area a wash part bottom (9) having through-openings, and two mounting areas each for receiving a filter (1) of flexible flat material (2), wherein the filters (1) are located each at a front surface of the peripheral wall (8), two closure members (13) covering the wash basket (7) at the top and at the bottom, and the front surfaces of the peripheral wall (8) together with the closure members (13) forming cooperating clamping surfaces, extending along closed sealing lines and enabling clamping a seal (3) and a filtering flat material (2) in contact with the seal (3), wherein the closure members (13) include each an area with through-openings covered by the filtering flat material (2) and surrounded by the sealing line, a groove (6) is formed at the closure members (13), or optionally at the wash basket (7), within a region of the sealing line wherein the seal (3), particularly a seal bond to the filtering flat material (2), is to be fixed in said groove (6), the tray further comprising clamping means which enables pressing the closure members against the corresponding front surface of the peripheral wall (8); and wherein the clamping means of the wash basket (7) and of each closure member (13) comprises cooperating engagement elements (12, 20), straps (12) projecting preferably from the peripheral wall (8) of the wash basket (7) to the exterior, and slider members (15) which include clamping surfaces (14) being movably supported such that the clamping surfaces (14) are movable along the straps (12) for achieving a desired contact position of the closure member (13) to the peripheral wall (8) and an elastic deformation of the filter seal (3).

\* \* \* \* \*